US006217769B1

(12) United States Patent
Okamoto et al.

(10) Patent No.: US 6,217,769 B1
(45) Date of Patent: Apr. 17, 2001

(54) SEPARATING AGENT FOR OPTICAL ISOMERS AND PROCESS FOR PRODUCING THE SAME

(75) Inventors: Yoshio Okamoto; Eiji Yashima, both of Aichi (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/284,854
(22) PCT Filed: Sep. 29, 1998
(86) PCT No.: PCT/JP98/04367
§ 371 Date: Apr. 19, 1999
§ 102(e) Date: Apr. 19, 1999
(87) PCT Pub. No.: WO99/18052
PCT Pub. Date: Apr. 15, 1999

(30) Foreign Application Priority Data

Oct. 3, 1997 (JP) .................................................. 9-271064
Sep. 21, 1998 (JP) ................................................ 10-266644

(51) Int. Cl.$^7$ .................................................. B01D 15/08
(52) U.S. Cl. ..................... 210/635; 210/656; 210/198.2; 210/502.1; 96/101; 502/404
(58) Field of Search ..................................... 210/634, 635, 210/656, 198.2, 502.1; 96/101; 428/403, 404, 407; 502/402, 404; 536/30, 55.1, 56, 58

(56) References Cited

U.S. PATENT DOCUMENTS

| 4,818,394 | * | 4/1989 | Okamoto | 210/198.2 |
| 5,772,876 | * | 6/1998 | Murakami | 210/198.2 |
| 5,906,734 | * | 5/1999 | Girot | 210/198.2 |
| 5,965,026 | * | 10/1999 | Oda | 210/198.2 |
| 6,039,876 | * | 3/2000 | Yang | 210/198.2 |
| 6,117,325 | * | 9/2000 | Oda | 210/198.2 |

FOREIGN PATENT DOCUMENTS

| 64-26523 | * | 1/1989 | (JP) | 210/198.2 |
| 5-43483 | * | 2/1993 | (JP) | 210/198.2 |
| 9-194399 | * | 7/1997 | (JP) | 210/198.2 |

* cited by examiner

Primary Examiner—Ernest G. Therkorn
(74) Attorney, Agent, or Firm—Flynn, Thiel, Boutell & Tanis, P.C.

(57) ABSTRACT

The invention provides separating agents for optical isomers which have a high optical resolving power inherent in polysaccharide derivatives and high solvent resistance, and which can be produced through short process steps; a process for producing the same, and a method for separating optical isomers. The invention also provides separating agents for optical isomers, wherein the surface of a polysaccharide derivative supported on a carrier or the surface of a pulverized or granulated polysaccharide derivative is coated with a polymer, which are produced by supporting the polysaccharide derivative on the carrier and then coating the surface thereof with the polymer to thereby immobilize the polysaccharide derivative on the substrate, or by grinding or spheroidizing the polysaccharide derivative and then coating the surface thereof with a polymer.

13 Claims, No Drawings

SEPARATING AGENT FOR OPTICAL ISOMERS AND PROCESS FOR PRODUCING THE SAME

REFERENCE TO RELATED APPLICATIONS

This application is a 371 of PCT/JP98/04367 filed Sep. 29, 1998.

TECHNICAL FIELD

This invention relates to separating agents for optical isomers, a process for producing the same, and a method for separating optical isomers. More particularly, it relates to separating agents which are useful in separating optical isomers and which are obtained by coating the surface of a polysaccharide derivative with a polymer to thereby immobilize the polysaccharide derivative on a carrier or to make the polysaccharide derivative alone solvent-resistant, a process for producing the same, and a method for separating optical isomers with the use of the same.

BACKGROUND ART

It has been well known that polysaccharides and derivatives thereof such as ester or carbamate derivatives of cellulose or amylose show a high optical resolving power. It has been also well known that chromatographic separating agents wherein these substances are physically adsorbed or held on silica gel are excellent separating agents having an optical resolving power over a wide range, a good theoretical plate number and a good durability (Y. Okamoto, M. Kawashima and K. Hatada, J. Am. Chem. Soc., 106, 5357, (1984)).

However, these separating agents can be employed only under restricted separation conditions, since polysaccharide derivatives are held on silica gel via physical adsorption and thus solvents in which the polysaccharide derivatives are soluble cannot be used as the mobile phase, etc. Also, solvents in which samples are to be dissolved are restricted. In the case of a sample having a low solubility in solvents usable as the mobile phase, there arises a serious problem particularly in chromatographic separation. Moreover, there is another inconvenience that only limited washing fluids are usable in washing away contaminants strongly adsorbed on the separating agents. Considering these points, there have been required separating agents carrying polysaccharide derivatives thereon and having a high solvent resistance.

To solve these problems, there have been developed a method wherein polysaccharide derivatives are chemically bonded directly to silica gel, a method wherein polysaccharide derivative molecules are crosslinked with each other and a method wherein a high solvent resistance is established by combining these two methods (JP-A 62-270602, JP-A 4-202141, JP-A 7-25904, JP-A 7-138301, JP-A 8-59702, WO95/18833, WO96/27615, WO97/4011 and WO97149733).

However, these techniques have the disadvantage of necessitating multi-step production processes, since unreacted hydroxyl or polyfunctional groups should be incorporated onto substituents for crosslinking or chemically bonding polysaccharide derivatives.

Accordingly, it has been required to develop separating agents for optical isomers which have the high optical resolving power inherent in polysaccharide derivatives together with a high solvent resistance and which can be produced through short process steps.

DISCLOSURE OF INVENTION

The present inventors have conducted extensive studies on separating agents for optical isomers which have the high optical resolving power inherent in polysaccharide derivatives and a high solvent resistance and which can be produced through short process steps and consequently completed the present invention.

Accordingly, the present invention provides a separating agent for optical isomers characterized in that the surface of a polysaccharide derivative supported on a carrier is coated with a polymer and a process for producing the same.

The present invention further provides a separating agent for optical isomers characterized in that the surface of a pulverized or granulated polysaccharide derivative is coated with a polymer and a process for producing the same.

The present invention furthermore provides a method for separating optical isomers characterized by using the above separating agents or the use of the above separating agents in separating optical isomers.

DETAILED DESCRIPTION OF THE INVENTION

Now, the mode for carrying out the present invention will be described in detail.

The polysaccharides to be used in the present invention may be any of synthetic polysaccharides and optionally modified natural ones, so long as they are optically active. It is preferable to use those having a regular binding mode. Examples thereof include $\beta$-1,4-glucan(cellulose), $\alpha$-1,4-glucan(amylose, amylopectin), $\alpha$-1,6-glucan(dextran), $\beta$-1,6-glucan(pustulan), $\beta$-1,3-glucan(curdlan, schizophyllan, etc.), $\alpha$-1,3-glucan, $\beta$-1,2-glucan(crown gall polysaccharides), $\beta$-1,4-galactan, $\beta$-1,4-mannan, $\alpha$-1,6-mannan, $\beta$-1,2-fructan (inulin), $\beta$-2,6-fructan (levan), $\beta$-1,4-xylan, $\beta$-1,3-xylan, $\beta$-1,4-chitosan, $\alpha$-1,4-N-acetylchitosan (chitin), pullulan, agarose and alginic acid. Also, starches containing amylose are included therein. Among these polysaccharides, it is preferable to use cellulose, amylose, $\beta$-1,4-xylan, $\beta$-1,4-chitosan, chitin, $\beta$-1,4-mannan, inulin, curdlan, etc. which can be easily obtained as highly pure polysaccharides, still preferably cellulose and amylose.

It is preferable that such a polysaccharide has a number-average degree of polymerization (i.e., the average number of pyranose or furanose rings per molecule) of at least 5, still preferably at least 10. From the viewpoint of handling properties, it is preferable that the number-average degree of polymerization thereof is not more than 500, though the upper limit thereof is not particularly defined.

Examples of the polysaccharide derivative to be used in the present invention include compounds prepared by introducing, into a portion of the hydroxyl groups of the above-mentioned polysaccharide, compounds having functional groups capable of reacting with the hydroxyl groups via ester, urethane or ether bonds by conventionally known methods. The compounds having functional groups capable of reacting with the hydroxyl groups may be isocyanic acid derivatives, carboxylic acids, esters, acid halides, acid amides, halides, epoxy compounds, aldehydes, alcohols and any other compounds having leaving groups. As these compounds, use can be made of aliphatic, alicyclic, aromatic and heteroaromatic ones. Among these compounds, those represented by the following general formula (I) are particularly preferable:

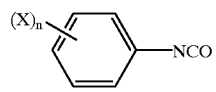

(I)

wherein X represents halogeno or $C_{1-3}$ alkyl; and n is a number of from 1 to 3.

Particularly preferable examples of the polysaccharide derivative to be used in the present invention include ester and carbamate derivatives of polysaccharides having at least 0.1 ester or urethane bond per monosaccharide.

As the carrier to be used in the present invention, use may be made of organic porous substrates and inorganic porous ones. It is preferred to use inorganic porous ones. Appropriate examples of the organic porous substrates include polymers comprising polystyrene, polyacrylamide, polyacrylate, etc. Appropriate examples of the inorganic porous substrates include silica, alumina, magnesia, glass, kaolin, titanium oxide, silicates and hydroxyapatite. Silica gel may be cited as a particularly preferable carrier. The particle diameter of the carrier is from 0.1 μm to 10 mm, preferably from 1 μm to 300 μm and the average pore size thereof is from 10 Å to 100 μm, preferably from 50 Å to 50,000 Å. When silica gel is employed as the carrier, it is preferable to preliminarily surface-coat the silica gel so as to exterminate the effects of the silanol remaining therein, though a non-surface-treated one may be used without any problem.

The separating agents for optical isomers according to the present invention can be produced by a process which comprises supporting a polysaccharide derivative on a carrier and then coating the surface thereof with a polymer to thereby immobilize the polysaccharide derivative on the carrier, or a process which comprises grinding or spheroidizing a polysaccharide derivative and then coating the surface thereof with a polymer.

In immobilizing the polysaccharide derivative on the carrier in the present invention, it is necessary that the polysaccharide derivative is supported on the carrier before the polymer is formed on the polysaccharide derivative. The polysaccharide derivative is supported on the carrier preferably in an amount of from 1 to 100% by weight, still preferably from 5 to 60% by weight, based on the carrier.

In the present invention, the polysaccharide derivative may be pulverized or granulated by a conventional method. It is preferable that the pulverized or granulated polysaccharide derivative thus obtained is optionally dressed by classifying so as to give a uniform particle size. The particle diameter of the polysaccharide derivative preferably ranges from 0.1 μm to 10 mm, still preferably from 1 μm to 300 μm.

The polymer with which the surface of the polysaccharide derivative is coated in the present invention is optionally chemically bonded to the polysaccharide derivative or the carrier. To sustain the regular structure of the polysaccharide derivative and fully establish the high optical resolving power inherent in the polysaccharide derivative, however, it is preferable that the polymer is chemically bonded neither to the polysaccharide derivative nor to the carrier.

In the present invention, the surface of the polysaccharide derivative is coated with the polymer by, for example, a method which comprises polymerizing or copolymerizing polymerizable monomer(s) on the polysaccharide derivative to thereby form a polymer coating, or a method which comprises reacting, on the polysaccharide derivative, a polyfunctional crosslinking agent with a polyfunctional compound other than the polysaccharide derivative to thereby effect crosslinking.

Examples of the polymerizable monomers to be used in the present invention include vinylic hydrocarbon compounds such as styrene and divinylbenzene, methacrylic acid derivatives such as methacrylates and methacrylamide, acrylic acid derivatives such as acrylates and acyliamide, and silicon-containing compounds.

Examples of the polyfunctional crosslinking agent to be used in the present invention include diisocyanate derivatives, dicarboxylic acids or acid chlorides thereof, diepoxy derivatives and divinyl derivatives. Examples of the polyfunctional compound other than the polysaccharide derivative include those reacting with the polyfunctional crosslinking agent to give a polymer, such as polyols, polyamines and polythiol compounds.

Preferable examples of the polymer to be used in the present invention include homopolymers of the above-mentioned polymerizable monomers and copolymers consisting of two or more of the same. It is still preferable to use therefor copolymers of a polymerizable and non-crosslinkable monomer having one unsaturated double bond (for example, styrene, a methacrylic acid derivative or an acrylic acid derivative) with a polymerizable and crosslinkable monomer having at least two unsaturated double bonds (for example, divinylbenzene). It is particularly preferable to use a styrene-divinylbenzene copolymer therefor.

To form the polymer on the polysaccharide derivative in the present invention, it is desirable to preliminarily apply the polymerizable monomer or the polyfunctional compound onto the polysaccharide derivative. In this application step, the polymerizable monomer, if employed, may coexist with a reaction initiator such as a free-radical initiator. Alternatively, the initiator may be contained in a reaction solvent. It is also possible to initiate the polymerization reaction by heating or photoirradiation without resort to any initiator.

In the case of the polyfunctional compound, it may coexist with the polyfunctional crosslinking agent in the application step, or it may be contained in the reaction solvent.

To form the polymer coating on the polysaccharide derivative in the present invention, it is also possible to apply or chemically bond thereto the polymer per se such as polystyrene, a polyacrylic acid derivative, a polymethacrylic acid derivative, polyester, polyether or a polysilane compound.

The membrane of the polymer coating to be formed on the polysaccharide derivative in the present invention is not particularly restricted, so long as it can immobilize the polysaccharide derivative or make the same solvent-resistant while sustaining the high optical resolving power inherent in the polysaccharide derivative. However, it is preferable to use a porous membrane capable of controlling the permeation of substances therethrough depending on molecular size. It is particularly preferable to use a porous film selectively allowing the permeation of an optical isomer having a relatively low molecular weight while not allowing the permeation of a polysaccharide derivative having a high molecular weight to thereby immobilize them or make the same solvent-resistant.

To form such a porous film, it is preferable to use a copolymer consisting of a polymerizable and non-crosslinkable monomer having one unsaturated double bond and a polymerizable and crosslinkable monomer having at least two unsaturated double bonds as described above. It is still preferable to use one wherein a non-crosslinkable monomer is copolymerized with a crosslinkable monomer at a weight ratio of from 1/10 to 10/1.

The weight ratio of the polysaccharide derivative to these polymerizable monomers preferably ranges from 1/1 to 1/100.

The separating agents for optical isomers according to the present invention are useful as chromatographic separating agents to be used in gas chromatography, liquid chromatography, thin layer chromatography, etc. It is particularly preferable to use the same as separating agents in liquid chromatography.

The use of the separating agents of the present invention as chromatographic separating agents as described above makes it possible to efficiently separate various optical isomers.

The separating agents of the present invention have the high optical resolving power inherent in polysaccharide derivatives and high solvent resistance, which makes them useful in the separation of various optical isomers.

EXAMPLES

To further illustrate the present invention in greater detail, and not by way of limitation, the following Examples will be given.

Example 1

Synthesis of separating agent having cellulose tris (3,5-dimethylphenyl)carbamate immobilized on silica gel with the use of sytrene-divinylbenzene copolymer (1) Surface-treatment of silica gel A porous silica gel (SP-1000, mfd. by Daiso, particle diameter: 7 μm, average pore size: 1000 Å) was subjected to aminopropylsilane (APS) treatment in a conventional manner by reacting with 3-aminopropyltriethoxysilane.

(2) Synthesis of cellulose tris(3,5-dimethylphenyl) carbamate (CDMPC)

In a nitrogen atmosphere, 10 g of cellulose (Microcrystalline Avicel, mfd. by Merck & Co., Inc.) and 42 g of 3,5-dimethylphenyl isocyanate were heated at 100° C. under stirring for 48 hours in 100 ml of dry pyridine. Next, the reaction mixture was poured into 2 l of methanol. The solid thus precipitated was taken up by filtration through a glass filter and washed with methanol several times followed by vacuum drying (80° C., 5 hr).

(3) Supporting of cellulose carbamate derivative on silica gel 2.5 g of the cellulose tris(3,5-dimethylphenyl)carbamate obtained in the step (2) was dissolved in 20 ml of tetrahydrofuran (THF). The resultant polymer dope was applied uniformly onto 7.5 g of the APS-treated silica gel described in the step (1). After the completion of the application, the polymer dope of the polysaccharide derivative was allowed to sufficiently permeate into the silica gel pores and then THF was distilled off. The obtained silica gel supporting the polysaccharide derivative polymer thereon was washed with methanol followed by vacuum drying (80° C., 2 hr).

(4) Formation of polymer coating on silica gel supporting polysaccharide derivative polymer thereon and immobilization of polysaccharide derivative polymer Styrene (St) and divinylbenzene (DVB) were employed at the ratio as specified in Table 1 while azo-N,N'-bis (isobutyronitrile) (AIBN) was employed at a weight ratio AIBN/(St+DVB) of 1/50. St, DVB and AIBN were dissolved in dry hexane and the resultant solution of St-DVB-AIBN in hexane was uniformly sprinkled over 10 g of the silica gel supporting the polysaccharide derivative polymer thereon and prepared in the step (3).

After distilling off the hexane by air-drying for several hours, the residue was introduced into a flask and then polymerization was effected in a water bath at 60° C. for 20 hr.

The obtained polysaccharide derivative-immobilized separating agent was repeatedly washed with THF on a glass filter until neither the St-DVB copolymer nor the polysaccharide derivative polymer run down therefrom anymore. Then the polysaccharide derivative immobilization rate was calculated based on the weight of the solubles in the THF used in washing.

Finally, the separating agent was washed with methanol and vacuum-dried (80° C., 3 hr) to thereby give each of the five polysaccharide derivative-immobilized separating agents 1 to 5 as listed in Table 1.

Table 1 also shows the ratios of St, DVB and CDMPC employed in the separating agents 1 to 5 and the polysaccharide derivative immobilization rates of the immobilized separating agents.

TABLE 1

| Separating agent | (St + DVB)/ CDMPC (wt. %) | St/DVB (by wt.) | CDMPC/ separating agent (wt. %) | CDMPC immobilizn. rate (%) |
|---|---|---|---|---|
| Separating agent 1 | 20 | 1/1 | 16.1 | 85.8 |
| Separating agent 2 | 20 | 2/1 | 14.7 | 73.4 |
| Separating agent 3 | 30 | 1/1 | 18.1 | 96.8 |
| Separating agent 4 | 30 | 2/1 | 14.0 | 74.6 |
| Separating agent 5 | 40 | 1/1 | 16.1 | 86.1 |

Example 2

Synthesis of separating agent having cellulose tris (3,5-dimethylphenyl)carbamate immobilized on silica gel with the use of sytrene-divinylbenzene copolymer (1) Surface-treatment of silica gel A porous silica gel was subjected to the APS treatment in the same manner as the one described in Example 1(1).

(2) Synthesis of cellulose tris(3,5-dimethylphenyl) carbamate (CDMPC)

Cellulose tris(3,5-dimethylphenyl)carbamate was obtained in the same manner as the one described in Example 1(2).

(3) Supporting of cellulose carbamate derivative on silica gel 2.0 g of the cellulose tris(3,5-dimethylphenyl)carbamate obtained in the step (2) was supported on 8.0 g of the APS-treated silica gel obtained in the step (1) by using the same technique as the one described in Example 1(3).

(4) Formation of polymer coating on silica gel supporting polysaccharide derivative polymer thereon and immobilization of polysaccharide derivative polymer:

St and DVB were employed at the ratio as specified in Table 2 while AIBN was employed at a weight ratio AIBN/(St+DVB) of 1/25. St, DVB and AIBN were dissolved in 1.0 ml of dry toluene and the resultant solution of St-DVB- AIBN in toluene was uniformly sprinkled over 5 g of the silica gel supporting the polysaccharide derivative polymer thereon and prepared in the step (3).

In a nitrogen atmosphere, the reaction mixture was introduced into a flask and then polymerization was effected in an oil bath at 85° C. for 70 hr while stirring at about 30 rpm with the use of a mechanical stirrer.

The obtained polysaccharide derivative-immobilized separating agent was repeatedly washed with acetone on a glass filter until neither the St-DVB copolymer nor the polysaccharide derivative polymer run down therefrom any more. Then the polysaccharide derivative immobilization rate was calculated based on the weight of the solubles in the acetone used in washing.

Finally, the separating agent was washed with methanol and vacuum-dried (80° C., 3 hr) to thereby give each of the three polysaccharide derivative-immobilized separating agents 6 to 8 as listed in Table 2.

Table 2 also shows the ratios of St, DVB and CDMPC employed in the separating agents 6 to 8 and the polysaccharide derivative immobilization rates of the immobilized separating agents.

TABLE 2

| Separating agent | (St + DVB)/ CDMPC (wt. %) | St/DVB (by wt.) | CDMPC/ separating agent (wt. %) | CDMPC immobilizn. rate (%) |
| --- | --- | --- | --- | --- |
| Separating agent 6 | 30 | 1/1 | 20 | 100 |
| Separating agent 7 | 20 | 1/1 | 19.2 | 84 |
| Separating agent 8 | 10 | 1/2 | 7.6 | 28 |

Example 3

Synthesis of separating agent having cellulose tris (3,5-dimethylphenyl)carbamate immobilized on silica gel with the use of sytrene-divinylbenzene copolymer (1) Surface-treatment of silica gel A porous silica gel was subjected to the APS treatment in the same manner as the one described in Example 1(1).

(2) Synthesis of cellulose tris(3,5-dimethylphenyl) carbamate (CDMPC)

Cellulose tris(3,5-dimethylphenyl)carbamate was obtained in the same manner as the one described in Example 1(2).

(3) Supporting of cellulose carbamate derivative on silica gel

The cellulose tris(3,5-dimethylphenyl)carbamate obtained in the step (2) was immobilized on the APS-treated silica gel obtained in the step (1) by using the same technique as the one described in Example 1(3).

(4) Formation of polymer coating on silica gel supporting polysaccharide derivative polymer thereon and immobilization of polysaccharide derivative polymer:

St and DVB were employed at a weight ratio of 1/1 while AIBN was employed at a weight ratio AIBN/(St+DVB) of 1/25. St, DVB and AIBN were dissolved in 1.0 ml of dry toluene and the resultant solution of St-DVB-AIBN in toluene was uniformly sprinkled at a ratio (St+DVB)/ CDMPC of 30% by weight over 5 g of the silica gel supporting the polysaccharide derivative polymer thereon and prepared in the step (3).

In a nitrogen atmosphere, an aqueous solution prepared by adding several drops of polyoxyethylene (20) sorbitan laurate to 50 ml of purified water was poured into a flask. Next, the above silica gel supporting the polysaccharide derivative polymer onto which the St-DVB-AIBN-toluene solution had been uniformly sprinkled was well dispersed in the aqueous solution. Then polymerization was effected in an oil bath at 85° C. for 70 hr while stirring at about 75 rpm with the use of a mechanical stirrer.

The obtained polysaccharide derivative-immobilized separating agent was sufficiently washed with purified water on a glass filter and then repeatedly washed with acetone until neither the St-DVB copolymer nor the polysaccharide derivative polymer run down therefrom any more. Then the polysaccharide derivative immobilization rate was calculated based on the weight of the solubles in the acetone used in washing.

Finally, the separating agent was washed with methanol and vacuum-dried (80° C., 3 hr) to thereby give a polysaccharide derivative-immobilized separating agent (hereinafter referred to as the separating agent 9).

As a result, it was found that the obtained separating agent 9 showed a CDMPC/separating agent ratio of 19% by weight and a CDMPC immobilization rate of 90%.

Comparative Example 1

Preparation of separating agent having cellulose tris (3,5-dimethylphenyl)carbamate supported on silica gel via physical adsorption A separating agent wherein cellulose tris(3,5-dimethylphenyl)carbamate was supported on silica gel via physical adsorption was obtained by using the same method as the one employed in supporting the cellulose carbamate derivative on silica gel in Example 1(3).

Namely, 2.5 g of the cellulose tris(3,5-dimethylphenyl) carbamate obtained in the synthesis of the cellulose tris(3, 5-dimethylphenyl)carbamate (CDMPC) in Example 1(2) was dissolved in 20 ml of tetrahydrofuran (THF). The resultant polymer dope was then applied uniformly onto 7.5 g of the APS-treated silica gel obtained in Example 1(1). After the completion of the application, the polymer dope of the polysaccharide derivative was allowed to sufficiently permeate into the silica gel pores and then the THF was distilled off. The obtained silica gel supporting the polysaccharide derivative polymer thereon was washed with methanol followed by vacuum drying (80° C., 2 hr) to thereby give a separating agent (hereinafter referred to as the comparative separating agent 1).

Comparative Example 2

Preparation of Separating Agent Having Polysaccharide Derivative Immobilized on Silica Gel by Crosslinking Polysaccharide Derivative Molecules with Each Other and Polysaccharide Derivative with Silica Gel 1.8 g of tritylcellulose wherein about from 0.9 to 1.0 trityl group had been reacted per glucose unit was dissolved in THF. The resultant solution was then sprinkled uniformly over 6.0 g of the APS-treated silica gel obtained in Example 1(1). Next, the solvent was distilled off to thereby support the tritylcellulose on the silica gel. Then 75 ml of methanol and 0.75 ml of conc. hydrochloric acid were added thereto and the resultant mixture was allowed to stand at room temperature overnight to thereby eliminate the trityl groups.

After taking up by filtration, the obtained precipitate was washed with methanol. Then 75 ml of methanol and 0.75 ml of triethylamine were added thereto and the resultant mixture was stirred for 5 min. After taking up by filtration again, the precipitate was washed with methanol followed by vacuum drying (80° C., 3 hr).

In a nitrogen atmosphere, a solution of 49.3 mg of 4,4'-diphenylmethane diisocyanate dissolved in 6.5 ml of dry toluene was added to 3.4 g of the silica gel having cellulose adsorbed thereon obtained above. Further, 2.5 ml of dry pyridine was added thereto and the mixture was heated to 60° C. while stirring. After 5 hr, 20 ml of dry pyridine was poured thereinto and then 0.75 ml of 3,5-dimethylphenyl isocyanate was added thereto followed by heating to 110° C. After 18 hr, the precipitate was taken up by filtering through a glass filter and washed successively with THF, methanol, ethanol and hexane followed by vacuum drying (80° C., 3 hr). Thus a separating agent wherein the polysaccharide derivative had been immobilized on the silica gel by crosslinking both polysaccharide derivative molecules with each other and the polysaccharide derivative with the silica gel was obtained (hereinafter referred to as the comparative separating agent 2). The cellulose was supported on the silica gel at a ratio of about 18% (calculated by assuming that 2.5 hydroxyl groups among three in a glucose unit in the cellulose had been carbamoylated).

Comparative Example 3

Preparation of Separating Agent Having Polysaccharide Derivative Immobilized on Silica Gel Exclusively by Crosslinking Polysaccharide Derivative Molecules with Each Other (1) Inactivation of silica gel surface 200 g of the APS-treated silica gel obtained in Example 1(1) was reacted with 15 ml of 3,5-dimethylphenyl isocyanate in 1.0 l of methylene chloride at room temperature for 1.5 hr. The obtained product was taken up by filtration and then washed successively with methylene chloride/methanol (2/1), methylene chloride, ethanol, acetone and hexane followed by vacuum drying.

(2) Synthesis of cellulose 6-hydroxy-2,3-bis(3,5-dimethylphenyl isocyanate)

In a nitrogen atmosphere, 4.0 g of tritylcellulose wherein about from 0.9 to 1.0 trityl group had been reacted per glucose unit was dissolved in dry pyridine. Then 10 ml of 3,5-dimethylphenyl isocyanate was added thereto and the resultant mixture was heated to 100° C. and stirred for 25 hr. After pouring 700 ml of methanol thereinto, the solid matter thus precipitated was taken up by filtration, washed with ethanol and hexane, and then dried. Next, it was stirred in methanol containing conc. hydrochloric acid to thereby eliminate the trityl groups. The solid matter was taken up by filtration, washed with ethanol and hexane, and dried to give cellulose-6-hydroxy-2,3-bis(3,5-dimethylphenyl isocyanate).

(3) Preparation of silica gel having cellulose derivatives supported thereon:

1.5 g of the cellulose derivative obtained in the step (2) was dissolved in 8 ml of THF. The resultant solution was applied to 5.7 g of the surface-inactivated silica gel obtained in the step (1) by uniformly sprinkling. After distilling off the solvent, the residue was washed successively with methanol, ethanol and hexane to give silica gel having the cellulose derivative supported thereon.

(4) Immobilization of cellulose derivative on silica gel exclusively by crosslinking among cellulose derivative molecules:

35 ml of dry toluene was added to 6.7 g of the silica gel having the cellulose derivative supported thereon as obtained in the step (3). Further, 110 mg of diphenylmethane diisocyanate was added thereto and the resultant mixture was stirred at 110° C. for 6 hr. After the completion of the reaction, the precipitate was taken up by filtration and washed successively with THF, methanol, ethanol and hexane followed by vacuum drying to give a separating agent wherein the cellulose derivative had been immobilized on the silica gel exclusively by crosslinking the cellulose derivative molecules with each other.

(5) Modification of unreacted hydroxyl groups in polysaccharide derivative immobilized on silica gel:

To the separating agent obtained in the above (4) were added 25 ml of dry toluene and 15 ml of dry pyridine. After further adding 0.5 ml of 3,5-dimethylphenyl isocyanate, the resultant mixture was heated to 110° C. while stirring for 15 hr. After the completion of the reaction, the product was taken up by filtration and washed successively with THF, methanol, ethanol and hexane followed by vacuum drying to thereby carbamoylate the unreacted hydroxyl groups in the polysaccharide derivative immobilized on the silica gel, thus giving a separating agent (hereinafter referred to as the comparative separating agent 3). The cellulose was supported on the silica gel at a ratio of about 19% (calculated by assuming that 2.5 hydroxyl groups among three in a glucose unit in the cellulose had been carbamoylated).

Application Example 1

The separating agents 1 to 5 prepared in Example 1 and the comparative separating agent 1 prepared in Comparative Example 1 were each employed as a packing material and packed in a stainless column of 25 cm in height and 0.46 cm in inner diameter by the slurry packing method to give a column for separating optical isomers.

By using this column, various racemic modifications as listed in Table 3 were optically resolved by the liquid chromatographic technique under the following analytical conditions; mobile phase: hexane/2-propanol (90/10), flow velocity: 0.1 ml/min, temperature: 25° C., detection: at 254 nm. Table 3 summarizes the results wherein the separation factor ($\alpha$) means a value determined in accordance with the following formula.

$$\text{Separation factor } (\alpha) = \frac{\text{volume ratio of antipode adsorbed more strongly}}{\text{volume ratio of antipode adsorbed more weakly.}}$$

TABLE 3

| | Separating agent Separation factor ($\alpha$) | | | | | |
| --- | --- | --- | --- | --- | --- | --- |
| Racemic modification | Sepq. agent 1 | Sepq. agent 2 | Sepq. agent 3 | Sepq. agent 4 | Sepq. agent 5 | Comp. Sepq. agent 1 |
| Racemic modification 1 *1 | 1.25 | 1.32 | 1.18 | 1.24 | 1.14 | 1.32 |
| Racemic modification 2 *2 | 1.86 | 1.82 | 1.88 | 1.75 | 1.88 | 1.68 |
| Racemic modification 3 *3 | 2.73 | 3.12 | 2.79 | 2.65 | 2.67 | 2.59 |

TABLE 3-continued

| Racemic modification | Separating agent Separation factor (a) | | | | | |
|---|---|---|---|---|---|---|
| | Sepq. agent 1 | Sepq. agent 2 | Sepq. agent 3 | Sepq. agent 4 | Sepq. agent 5 | Comp. Sepq. agent 1 |
| Racemic modification 4 *4 | 1.17 | 1.25 | 1.21 | 1.23 | 1.22 | 1.34 |
| Racemic modification 5 *5 | Ca. 1 | Ca. 1 | Ca. 1 | Ca. 1 | Ca. 1 | Ca. 1 |
| Racemic modification 6 *6 | 1.24 | 1.15 | 1.14 | 1.18 | 1.12 | 1.15 |
| Racemic modification 7 *7 | 1.29 | 1.27 | 1.25 | 1.25 | 1.21 | 1.41 |
| Racemic modification 8 *8 | 1.42 | 1.43 | 1.51 | 1.40 | 1.44 | 1.58 |
| Racemic modification 9 *9 | 1.99 | 2.13 | 2.02 | 2.16 | 2.03 | 3.17 |
| Racemic modification 10 *10 | 2.27 | 3.12 | 2.01 | 2.50 | 2.08 | 1.83 |

Note)
*1 racemic modification 1

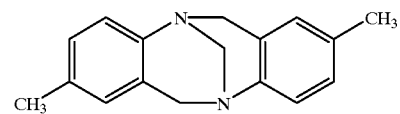

*2 racemic modification 2

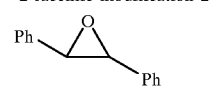

*3 racemic modification 3

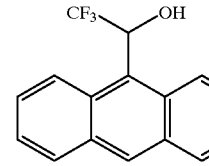

*4 racemic modification 4

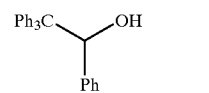

*5 racemic modification 5
Co(CH₃COCH₂CO)₃
*6 racemic modification 6

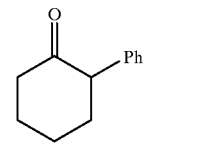

*7 racemic modification 7

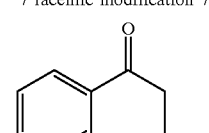

*8 racemic modification 8

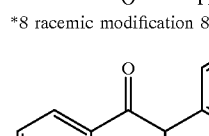

*9 racemic modification 9

*10 racemic modification 10

In the above series of formulae, Ph represents phenyl and Me represents methyl.

Application Example 2

The comparative separating agent 2 prepared in Comparative Example 2 was employed as a packing material and packed in a stainless column of 10 cm in height and 0.46 cm in inner diameter by the slurry packing method to give a column for separating optical isomers.

By using this column, various racemic modifications as listed in Table 4 were optically resolved by the liquid chromatographic technique.

The analytical conditions employed were as follows; mobile phase: hexane/2-propanol (90/10), flow velocity: 0.4 ml/min, temperature: 25° C., detection: at 254 nm. Table 4 shows the obtained results together with the data of the separating agent 2 according to the present invention achieving favorable results in Application Example 1.

Application Example 3

The comparative separating agent 3 prepared in Comparative Example 3 was employed as a packing material and packed in a stainless column of 25 cm in height and 0.46 cm in inner diameter by the slurry packing method to give a column for separating optical isomers.

By using this column, various racemic modifications as listed in Table 4 were optically resolved by the liquid chromatographic technique.

The analytical conditions employed were as follows; mobile phase: hexane/2-propanol (90/10), flow velocity: 1.0 ml/min, temperature: 25° C., detection: at 254 nm. Table 4 shows the obtained results.

TABLE 4

| | Separation factor (α) Separating agent | | |
|---|---|---|---|
| Racemic modification | Sepg. agent 1 | Comp. sepg. agent 2 | Comp. sepg. agent 3 |
| Racemic modification 1 *1 | 1.32 | 1.30 | 1.61 |
| Racemic modification 3 *1 | 3.12 | 1.55 | 2.06 |

TABLE 4-continued

| Racemic modification | Separation factor (α) Separating agent | | |
|---|---|---|---|
| | Sepg. agent 1 | Comp. sepg. agent 2 | Comp. sepg. agent 3 |
| Racemic modification 6 *1 | 1.15 | 1.14 | 1.25 |
| Racemic modification 7 *1 | 1.27 | 1.0 | 1.13 |
| Racemic modification 8 *1 | 1.43 | 1.0 | 1.16 |

Note)
*1: use was made of the same racemic modification as employed in Table 3.

Application Example 4

The separating agents 6 to 9 prepared in Examples 2 and 3 were each employed as a packing material and a column for separating optical isomers was prepared in the same manner as the one employed in Application Example 1.

By using this column, various racemic modifications as listed in Table 5 were optically resolved by the liquid chromatographic technique under the following analytical conditions; mobile phase: hexane/2-propanol (90/10), flow velocity: 1.0 ml/min, temperature: 25° C., detection: at 254 nm. Table 5 summarizes the results.

TABLE 5

| Racemic modification | Separation factor (α) Separating agent | | | |
|---|---|---|---|---|
| | Sepg. agent 6 | Sepg. agent 7 | Sepg. agent 8 | Sepg. agent 9 |
| Racemic modification 1 *1 | 1.29 | 1.43 | 1.31 | 1.24 |
| Racemic modification 2 *1 | 1.36 | 1.33 | 1.42 | 1.72 |
| Racemic modification 3 *1 | 2.31 | 2.21 | 2.23 | 2.45 |
| Racemic modification 5 *1 | 1.0 | 1.0 | 1.0 | 1.0 |
| Racemic modification 6 *1 | 1.19 | 1.22 | 1.15 | 1.15 |
| Racemic modification 7 *1 | 1.17 | 1.21 | 1.35 | 1.19 |
| Racemic modification 8 *1 | 1.54 | 1.44 | 1.61 | 1.40 |

Note)
*1: use was made of the same racemic modification as employed in Table 3.

Application Example 5

The separating agent 6 prepared in Example 2 and the comparative separating agent 1 prepared in Comparative Example 1 were each employed as a packing material and a column of 25 cm in height and 1.0 cm in inner diameter for separating optical isomers was prepared in the same manner as the one employed in Application Example 1.

By using this column, each mobile phase solvent as defined below was passed therethrough under the conditions as specified below and the amount of the matter eluted from the packing material was determined by the following method. Table 6 shows the result.

<Column Pass Conditions>
(1) Hexane/2-propanol: 90/10, flow velocity: 4.7 ml/min, temperature: 25° C., total volume of eluent: 1.2 l.
(2) Hexane/denatured ethanol {a solvent obtained by denaturing ethanol with 2-propanol (comprising 85.5% of ethanol, 13.4% of 2-propanol and 1.1% of methanol)}: 75/25, flow velocity: 4.7 ml/min, temperature: 40° C., total volume of eluent: 1.2 l.

The eluents (1) and (2) were passed successively.

<Method for Determining Eluted Matter>
The solvent was distilled off from the eluate obtained from the column by using an evaporator under a reduced pressure of about 20 mmHg at a water temperature of 40° C. and the concentrated residue thus obtained was weighed.

TABLE 6

| Eluent passed | Amount of eluted matter (g) Separating agent | |
|---|---|---|
| | Sepq. agent 6 | Com. sepq. agent 1 |
| (1) Hexane/2-propanol: 90/10 | 0.9 | 12.8 |
| (2) Hexane/denatured ethanol: 75/25 | 0.9 | 7.2 |

What is claimed is:

1. A separating agent for optical isomers, characterized in that an optically active polysaccharide derivative supported on a carrier is coated with a polymer to immobilize the polysaccharide derivitive on the carrier.

2. The separating agent for optical isomers as set forth in claim 1, wherein the particle diameter of the carrier is from 0.1 μm to 10 mm, while the pore size thereof is from 10 Å to 100 μm.

3. The separating agent for optical isomers as set forth in claim 1, wherein the polysaccharide derivative is an ester or carbamate derivative of a polysaccharide having at least 0.1 ester bond or urethane bond per monosaccharide unit.

4. The separating agent for optical isomers as set forth in claim 1, which is suitable for use in chromatography.

5. A process for producing the separating agent for optical isomers as set forth in claim 1, characterized by supporting the polysaccharide derivative on the carrier and then coating it with the polymer to thereby immobilize the polysaccharide derivative on the carrier.

6. The process as set forth in claim 5, characterized by polymerizing or copolymerizing a polymerizable monomer (s) on the polysaccharide derivative to form the polymer coating.

7. The process as set forth in claim 6, wherein the polymerizable monomer is at least one member selected from the group consisting of vinylic hydrocarbon compounds, methacrylic acid derivatives, acrylic acid derivatives and silicon-containing compounds.

8. The process as set forth in claim 5, characterized by reacting, on the polysaccharide derivative, a polyfunctional crosslinking agent with a polyfunctional compound other than the polysaccharide derivative to thereby effect crosslinking and to form the polymer coating.

9. The process as set forth in claim 8, wherein the polyfunctional crosslinking agent is at least one member selected from the group consisting of diisocyanate derivatives, dicarboxylic acids or acid chlorides thereof, diepoxy derivatives, and divinyl derivatives.

10. The process as set forth in claim 8, wherein the polyfunctional compound other than the polysaccharide derivative is at least one member selected from the group consisting of polyols, polyamines and polythiol compounds.

11. A method for separating optical isomers, characterized by separating the optical isomers with the separating agent as claimed in claim 1.

12. A separating agent for optical isomers, characterized in that a pulverized or granulated optically active polysaccharide derivative is coated with a polymer to make the polysaccharide derivative solvent resistant.

13. A process for producing the separating agent for optical isomers as set forth in claim 12, characterized by pulverizing or granulating the polysaccharide derivative and then coating it with the polymer.

* * * * *